(12) United States Patent
Kim et al.

(10) Patent No.: US 9,072,883 B2
(45) Date of Patent: Jul. 7, 2015

(54) BATTERY-INTEGRATED IONTOPHORESIS PATCH

(75) Inventors: Nam In Kim, Gwangju (KR); Myoung Woo Jung, Gwangju (KR); Seung Gyu Lim, Gwangju (KR); Kwang Suk Kim, Gwangju (KR)

(73) Assignee: ROCKET ELECTRIC CO., LTD. (KR)

( * ) Notice: Subject to any disclaimer, the term of this patent is extended or adjusted under 35 U.S.C. 154(b) by 745 days.

(21) Appl. No.: 12/936,633

(22) PCT Filed: Apr. 7, 2009

(86) PCT No.: PCT/KR2009/001780
§ 371 (c)(1),
(2), (4) Date: Oct. 6, 2010

(87) PCT Pub. No.: WO2009/125960
PCT Pub. Date: Oct. 15, 2009

(65) Prior Publication Data
US 2011/0034858 A1    Feb. 10, 2011

(30) Foreign Application Priority Data

Apr. 7, 2008    (KR) .......................... 10-2008-0032331

(51) Int. Cl.
*A61N 1/04*    (2006.01)

(52) U.S. Cl.
CPC .............. *A61N 1/0436* (2013.01); *A61N 1/044* (2013.01)

(58) Field of Classification Search
CPC ....... A61N 1/0436; A61N 1/044; A61N 1/30; A61N 1/303; A61N 1/0428; A61N 1/0424; A61N 1/0492; A61K 9/7084; A61K 9/7023; A61K 9/7092
USPC ......................................... 604/20, 890.1, 501
See application file for complete search history.

(56) References Cited

U.S. PATENT DOCUMENTS 4,927,408 A * 5/1990 Haak et al. ...................... 604/20
5,162,042 A * 11/1992 Gyory et al. .................... 604/20
(Continued)

FOREIGN PATENT DOCUMENTS

KR    1993-0000062    1/1993
KR    10-2008-0003814    1/2008
(Continued)

OTHER PUBLICATIONS

International Search Report—PCT/KR2009/001780 dated Nov. 25, 2009.

*Primary Examiner* — Nicholas Lucchesi
*Assistant Examiner* — Weng Lee
(74) *Attorney, Agent, or Firm* — Cantor Colburn LLP

(57) ABSTRACT

The present invention relates to an iontophoresis patch integrated with a battery, more specifically to an iontophoresis patch integrated with a battery which adopts the principle of iontophoresis as a means for infiltrating a substance of interest such as a medication or a cosmetic substance into skin. The iontophoresis patch of the invention comprises: a variable-shape substrate; a first electroconductive layer coming into contact with the substrate; a first electrode layer coming into contact with a part of the first electroconductive layer; a second electroconductive layer which comes into contact with the substrate and which is disposed on the same as the first electroconductive layer; a collector coming into contact with the second electroconductive layer; an electroconductive adhesive coming into contact with the second electroconductive layer and with the collector; a second electrode layer coming into contact with the collector and having a polarity opposite to that of the first electrode layer; an ion-conductive polymer electrolyte disposed between the first electrode layer and the second electrode layer; and an adhesive for sealing the ion-conductive polymer electrolyte.

20 Claims, 8 Drawing Sheets

(56) References Cited

U.S. PATENT DOCUMENTS

| | | | |
|---|---|---|---|
| 5,250,023 A | 10/1993 | Lee et al. | |
| 5,387,189 A * | 2/1995 | Gory et al. | 604/20 |
| 5,797,867 A * | 8/1998 | Guerrera et al. | 604/20 |
| 5,857,993 A * | 1/1999 | Atanasoska et al. | 604/20 |
| 5,871,461 A * | 2/1999 | Atanasoska et al. | 604/20 |
| 5,897,522 A | 4/1999 | Nitzan | |
| 5,947,920 A * | 9/1999 | Beck | 604/20 |
| 5,978,701 A * | 11/1999 | Johnson et al. | 604/20 |
| 6,086,572 A | 7/2000 | Johnson et al. | 604/503 |
| 6,259,946 B1 * | 7/2001 | Higo et al. | 604/20 |
| 6,355,025 B1 * | 3/2002 | Phipps et al. | 604/501 |
| 6,391,643 B1 * | 5/2002 | Chen et al. | 436/14 |
| 7,563,255 B2 * | 7/2009 | Adamis et al. | 604/294 |
| 2004/0267189 A1 * | 12/2004 | Mavor et al. | 604/20 |
| 2006/0023535 A1 | 2/2006 | Chun et al. | |
| 2007/0078373 A1 * | 4/2007 | Sharma et al. | 604/20 |
| 2008/0154179 A1 * | 6/2008 | Cantor et al. | 604/20 |
| 2009/0143761 A1 * | 6/2009 | Cantor et al. | 604/501 |
| 2010/0228180 A1 * | 9/2010 | Jayes et al. | 604/20 |
| 2012/0226219 A1 * | 9/2012 | Kim et al. | 604/20 |

FOREIGN PATENT DOCUMENTS

| | | |
|---|---|---|
| KR | 100816554 | 3/2008 |
| KR | 100868350 | 11/2008 |

* cited by examiner

BATTERY-INTEGRATED IONTOPHORESIS PATCH

TECHNICAL FIELD

The present invention relates to a battery-integrated iontophoresis patch, and, more particularly, to a battery-integrated iontophoresis patch which adopts an iontophoresis principle as a means for infiltrating a target substance such as a medicinal substance or a cosmetic substance into the skin.

BACKGROUND ART

Iontophoresis is a technology used to infiltrate a target substance having electric charge into the skin using electrical repulsion by allowing a micro current to flow in the skin.

When a patch mounted with the target substance is attached to the skin, a circuit in which an electric current can flow is formed in the skin, and thus electrical repulsion infiltrates the target substance into the skin. The infiltration rate of a target substance is known to be influenced by the amount of current flowing in the skin and the voltage.

A conventional iontophoresis patch is manufactured by independently fabricating a thin film-type battery and a patch mounted with an electroconductive electrode and then connecting the electroconductive electrode with the thin film-type battery. However, this conventional iontophoresis patch is problematic in that resistance increases when electric current flows, and in that an assembly process is complicated, and thus productivity becomes low, thereby increasing the manufacturing cost thereof.

In order to solve the problem, Korean Patent Registration No. 868350, filed by the present applicant, discloses an iontophoresis patch in which an electrode material is directly applied onto a conductive layer in the patch to form the patch and a battery into one system. The iontophoresis patch uses the conductive layer as the electrode of a battery and uses ion-conductive hydrogel to minimize the contact resistance between the patch and skin. However, this iontophoresis patch is also problematic in that a target substance having low electrochemical resistance is destroyed because it directly comes into contact with an electrode of a battery.

DISCLOSURE

[Technical Problem]

Accordingly, the present invention has been devised to solve the above-mentioned problems, and an object of the present invention is to provide an iontophoresis patch which can improve productivity by integrating a patch with a battery and which can increase the efficiency of infiltration by minimizing electrical resistance.

Another object of the present invention is to provide an iontophoresis patch to which a target substance having low electrochemical resistance can also be applied by preventing the target substance from participating in an electrode reaction and being destroyed.

[Technical Solution]

In order to accomplish the above objects, an aspect of the present invention provides an iontophoresis patch comprising: a variable-shape substrate; a first electroconductive layer coming into contact with the substrate; a first electrode layer coming into contact with a part of the first electroconductive layer; a second electroconductive layer which comes into contact with the substrate and which is disposed on the same plane as the first electroconductive layer; a collector coming into contact with the second electroconductive layer; an electroconductive adhesive coming into contact with the second electroconductive layer and with the collector; a second electrode layer coming into contact with the collector and having a polarity opposite to that of the first electrode layer; an ion-conductive polymer electrolyte disposed between the first electrode layer and the second electrode layer; and an adhesive for sealing the ion-conductive polymer electrolyte.

[Advantageous Effects]

The battery-integrated iontophoresis patch according to the present invention is advantageous in that it includes a first electroconductive layer, a first electrode layer, a second electroconductive layer, a second electrode layer and a polymer electrolyte, and the edges of the electrodes are sealed, so that an electrode material and a polymer electrolyte are isolated from the electroconductive layers, with the result that it is possible to prevent a target substance from participating in an electrode reaction and thus being destroyed, thereby increasing the efficiency of the iontophoresis patch and improving the productivity thereof as well as applying a target substance having low electrochemical resistance to the iontophoresis patch.

DESCRIPTION OF ELEMENTS IN THE DRAWINGS

Figure 1:
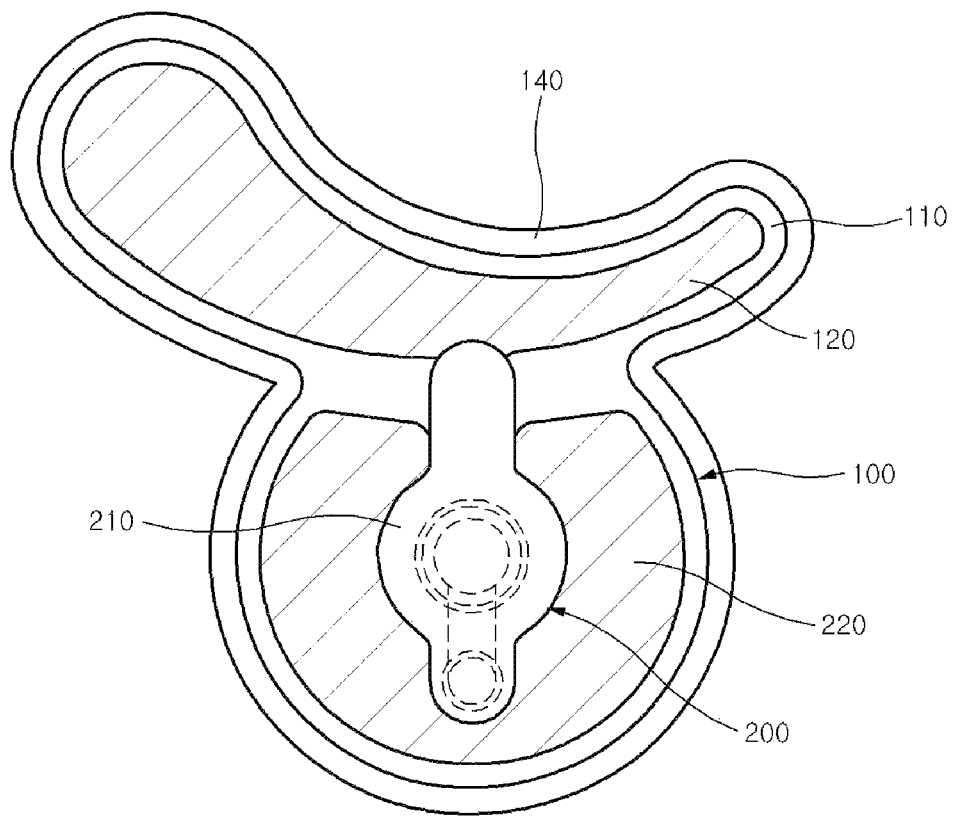
FIG. 1 is a plan view showing an iontophoresis patch according to the present invention.

110: substrate
100: first electrode unit
120: first electroconductive layer
130: first electrode layer
140: backing layer
200: second electrode unit
210: substrate
220: second electroconductive layer
230: second electrode layer
240: collector
250: electroconductive adhesive
260: adhesive
300: ion-conductive polymer electrolyte

BEST MODE

Hereinafter, preferred embodiments of the present invention will be described.

In the description of the present invention, when it is determined that the detailed description of the related art would obscure the gist of the present invention, the description thereof will be omitted. Further, the terms and words used in the present specification and claims should not be interpreted as being limited to typical meanings or dictionary definitions, but should be interpreted as having meanings and concepts relevant to the technical scope of the present invention based on the rule according to which an inventor can appropriately define the concept of the term to describe the best method he or she knows for carrying out the invention.

First, the battery-integrated iontophoresis patch according to the present invention includes: a variable-shape substrate; a first electroconductive layer coming into contact with the substrate; a first electrode layer coming into contact with a part of the first electroconductive layer; a second electroconductive layer which comes into contact with the substrate and which is disposed on the same plane as the first electroconductive layer; a collector coming into contact with the second electroconductive layer; an electroconductive adhesive coming into contact with the second electroconductive layer and with the collector; a second electrode layer coming into contact with the collector and having a polarity opposite to that of the first electrode layer; an ion-conductive polymer electrolyte disposed between the first electrode layer and the second electrode layer; and an adhesive for sealing the ion-conductive polymer electrolyte.

For the convenience of clearly understanding the present invention, the iontophoresis patch is divided into a first electrode unit 100 and a second electrode unit 200. However, the present invention is not limited thereto.

In the iontophoresis patch, the substrate is made of any one of polyethylene terephthalate and polyacrylonitrile.

Further, the first electroconductive layer includes any one of carbon powder and silver powder.

A part of the first electroconductive layer is coated with a slurry including an electric current generating material, a conducting material and a binder to form a first electrode layer, and the first electrode layer acts as a cathode.

Further, the first electrode layer includes manganese dioxide powder, carbon powder and a binder.

Here, the binder includes any one of polyethylene oxide, polyvinyl alcohol, polyvinyl pyrrolidone, polymethyl methacrylate and combinations thereof.

Further, the second electroconductive layer includes any one of carbon powder, silver powder and nickel powder.

Further, the collector includes carbon powder.

Further, the adhesive may be double-sided adhesive tape.

Further, the second electrode layer includes zinc powder, carbon powder and a binder.

Here, the binder includes any one of polyethylene oxide, polyvinyl alcohol, polyvinyl pyrrolidone, polymethyl methacrylate and combinations thereof.

Further, the ion-conductive polymer electrolyte includes any one of zinc chloride, ammonium chloride, sodium chloride and combinations thereof.

Further, the electroconductive adhesive includes any one of carbon powder, metal powder and combinations thereof.

The iontophoresis patch of the present invention further include a backing layer which has a variable shape such that it easily attaches to skin and which is made of an insulating material.

Hereinafter, preferred embodiments of the present invention will be described in detail. However, the present invention is not limited thereto.

The first electrode unit 100 includes a substrate 110, a first electroconductive layer 120 formed on the substrate 110, a first electrode layer 130 formed on the first electroconductive layer 120, a second electroconductive layer 220 disposed on the same plane as the first electroconductive layer 120, and a second electrode layer 230 electrically connected to the second electroconductive layer 220 and facing the first electrode layer 130. Here, an ion-conductive polymer electrolyte 300 is disposed between the first electrode layer 130 and the second electrode layer 230.

The first electroconductive layer 120 is formed by coating the substrate 110 with a conductive material including any one of carbon powder ink and silver powder ink.

A part of the first electroconductive layer 120 is coated with a slurry including an electric current generating material, a conducting material and a binder to form a first electrode layer 130, and the first electrode layer 130 acts as a cathode.

Manganese dioxide powder may be used as the electric current generating material, and carbon powder may be used as the conducting material. The binder may include any one of polyethylene oxide, polyvinyl alcohol, polyvinyl pyrrolidone, polymethyl methacrylate and combinations thereof.

The second electroconductive layer 220 may be made of the same material as the first electroconductive layer 120, and may be formed by coating the substrate 110 with a conductive material including any one of carbon powder ink, silver powder ink and nickel powder ink. The second electroconductive layer 220 is designed such that it is electrically separated from the first electroconductive layer 120.

The second electrode unit 200 includes a substrate 210 and a collector 240 which is formed on the substrate 210 and which is formed by applying carbon powder ink onto the substrate 210.

The second electrode unit 200 further includes a second electrode layer 230 which is formed by applying a slurry including an electric current generating material, a conducting material and a binder onto the collector 240 and which comes into contact with the collector 240. The second electrode layer acts as an anode.

Zinc powder may be used as the electric current generating material, and carbon powder may be used as the conducting material. The binder may include any one of polyethylene oxide, polyvinyl alcohol, polyvinyl pyrrolidone, polymethyl methacrylate and combinations thereof.

The electroconductive adhesive 250 serves to connect the collector 240 with the second electroconductive layer 220, and includes any one of carbon powder, metal powder and combinations thereof. Particularly, in the case of the first electrode layer 130 acting as a cathode and the second electrode layer 230 acting as an anode, the electroconductive adhesive 250 is used in a state of manganese dioxide powder and zinc powder to allow each of the first electrode layer 130 and the second electrode layer 230 to have high current density and to allow the manufacturing process to be convenient.

An ion-conductive polymer electrolyte 300 in which ions can flow is disposed between the first electrode layer 130 and the second electrode layer 230. The polymer electrolyte 300 is formed into a polymer-gel electrolyte by dissolving any one of polyethylene oxide, polyvinyl alcohol, polyvinyl pyrrolidone and combinations thereof in a water solution including any one of zinc chloride, ammonium chloride, sodium chloride and combinations thereof, and is wetted to non-woven fabric or kraft paper, and then used.

An adhesive 260 is disposed around the polymer electrolyte 300 in order to prevent the polymer electrolyte 300 from being volatilized and to attach the second electrode unit 200 to the iontophoresis patch. The adhesive 260 may be fabricated such that it has the same pattern as the second electrode unit 200. In this case, the site at which the polymer electrolyte and the electroconductive adhesive 250 will be disposed is cut out in order to correspond to the object of the present invention. The adhesive may be double-sided adhesive tape. The electroconductive adhesive 250 is disposed between the collector 240 and the second electroconductive layer 220 to induce electric current to flow.

The electrode material to be applied onto a part of the first electroconductive layer 120 is determined by the kind of electric charge of a target substance to be carried on the first electroconductive layer 120. When the target substance to be administered into the human body has a negative electric charge, an anode material is applied onto a part of the first electroconductive layer 120, and when the target substance has a positive electric charge, a cathode material is applied thereonto, thus causing electrical repulsion. It was described in an embodiment of the present invention that the first electrode layer acts as a cathode and the second electrode layer acts as an anode.

The operating principle of the present invention is that electric repulsion caused by electron flow (electric current) resulting from a cell reaction causes a polar target substance to infiltrate into the skin.

The iontophoresis patch is configured such that an electrolyte is disposed between the first electrode layer 130 directly applied onto the first electroconductive layer 120 and the second electrode layer 230 electrically connected to the second electroconductive layer 220, and a battery is isolated from a patch conductive layer by the adhesive 260.

When a target substance is carried on the first electroconductive layer 120 and then the iontophoresis patch is attached to the skin, a circuit is formed, so that the target substance infiltrates into the skin. Also, when the circuit is formed, electrons emitted from an anode pass through the collector 240 and the electroconductive adhesive 250 and are then formed into anions through a charge transfer process, and then the anions move into the skin from the first electroconductive layer 120. The anions moving into the skin generate electrons through a charge transfer process at the interface of the skin and the first electroconductive layer 120, and then the electrons move to a cathode to participate in a reduction reaction. In the same manner as this, cations move in the skin in a direction opposite to the flow of anions, thus allowing the target substance having the same polarity as the cations to move in the skin. In this case, the ions functioning like electrons move between a cathode and an anode by the medium of the polymer electrolyte 300 isolated by the adhesive 260

Therefore, according to the iontophoresis patch of the present invention, the increase in resistance occurring during electrical connection can be minimized because electrodes are formed right on the first electroconductive layer 120, and a target substance having low electrochemical resistance may also be applied because a target substance and electrodes are separated from each other. Further, the productivity of the iontophoresis patch can be improved because a patch and a battery can be manufactured in the same process.

Hereinafter, an embodiment of the present invention will be described with reference to the attached drawings.

FIG. 1 is a schematic plan view showing an iontophoresis patch according to the present invention. The iontophoresis patch is formed by attaching a second electrode unit 200 including a second electrode layer 230 and a collector 240 to a first electrode unit 100 including a first electroconductive layer 120 and a first electrode layer 130 and then sealing the second electrode unit 200 using an adhesive 260, which is double-sided adhesive tape.

In order to easily attach the iontophoresis patch to the skin, a substrate 110 is attached onto a backing layer 140 having a larger size than the substrate 110. In this case, a variety of differently shaped substrates can be used because the backing layer directly comes into contact with skin.

Figure 2:
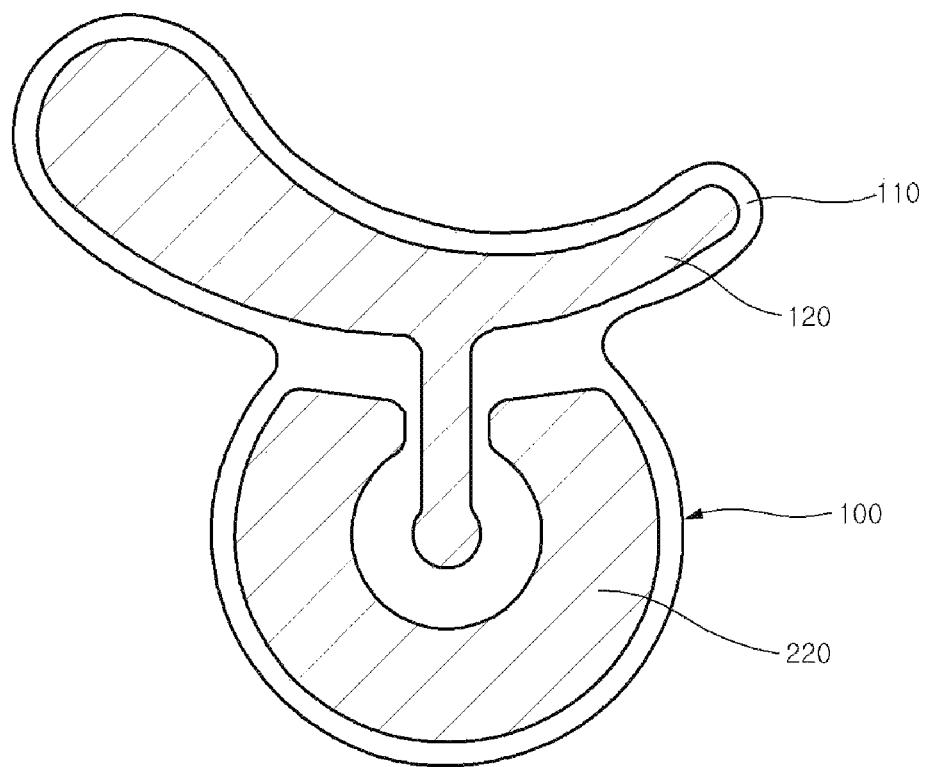
FIG. 2 is a plan view of a first electrode unit showing a first electroconductive layer and a second electroconductive layer.

FIG. 2 is a plan view of a first electrode unit 100 showing a first electroconductive layer 120 and a second electroconductive layer 220 formed on a substrate 110. A polyethylene terephthalate or polyacrylonitrile film may be used as the substrate 110. The substrate 110 is attached onto the backing layer 140.

In the first electroconductive layer 120 and the second electroconductive layer 220, silk printing, offset printing, evaporation, slurry coating or the like is performed using a slurry comprising metal or carbon powder and a polymer, such as carbon ink containing carbon powder or silver ink containing silver powder.

Carbon powder ink is printed on the substrate 110 and then dried to form an electroconductive layer having a thickness of about 15 µm. In this case, when the constituents of the first electroconductive layer 120 are the same as those of the second electroconductive layer 220, the layers can be formed at the same time.

Figure 3:
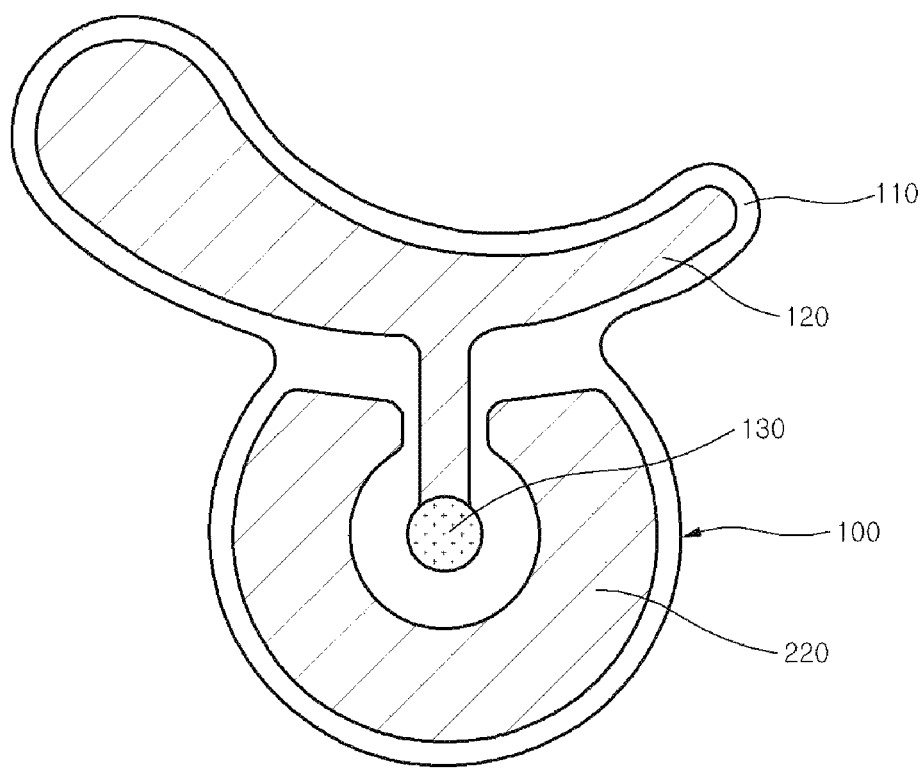
FIG. 3 is a plan view of a first electrode unit showing a first electrode layer.

FIGS. 2 and 3 are plan views showing a first electrode unit 100 including a first electrode layer 130 formed by coating the circular portion of the first electroconductive layer 120 surrounded by the second electroconductive layer 220 with a cathode composite material and then drying the cathode composite material. The cathode composite material includes manganese dioxide powder, carbon powder and a binder.

Various cathode active materials generating electric current were examined, but manganese dioxide may be preferably used as a cathode active material for the sake of electric capacitance, voltage, electrochemical characteristics, product distribution environments, and the like.

The binder included in the cathode composite material may include any one of polyethylene oxide, polyvinyl alcohol, polyvinyl pyrrolidone, 2-hydroxyethyl cellulose, polymethyl methacrylate and combinations thereof.

At the time of manufacturing an electrode, a multi-component binder system in which two or more kinds of binders are mixed is advantageous in terms of electrical efficiency, mechanical strength and adhesivity compared to a single kind of binder. In particular, as an electrode binder, a combination of polyethylene oxide and polymethyl methacrylate is excellent in terms of the durability and processability of an electrode.

Figure 4:
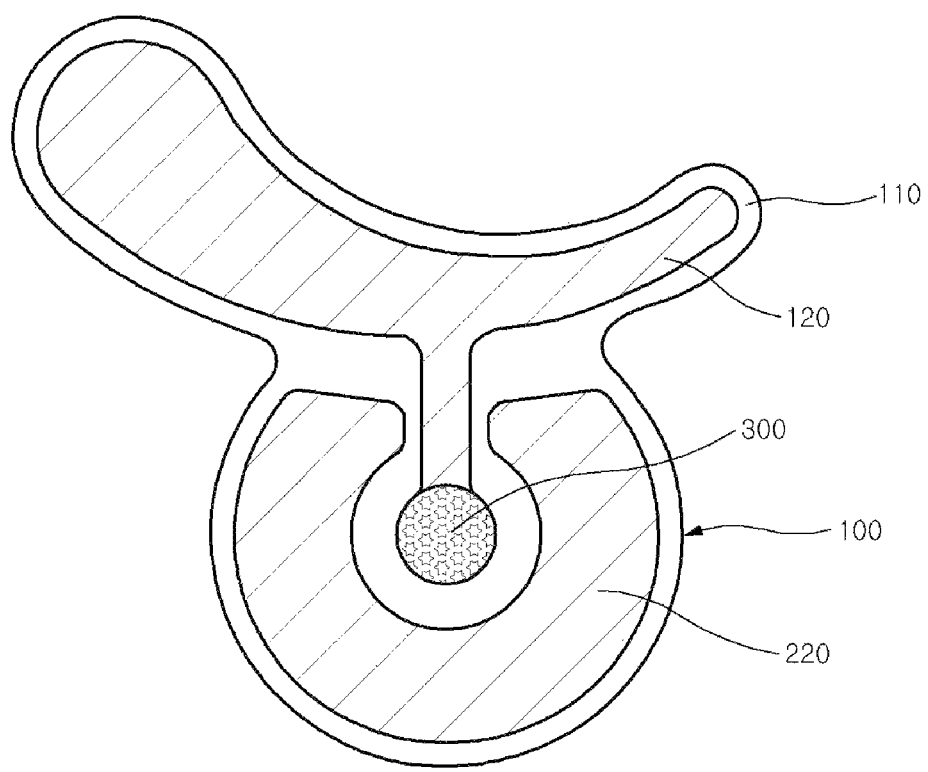
FIG. 4 is a plan view of a first electrode unit showing an ion-conductive polymer electrolyte.

FIG. 4 is a plan view showing a first electrode unit 100 in which an ion-conductive polymer electrolyte 300 is disposed on a first electrode layer 130. The ion-conductive polymer electrolyte 300 is formed into a polymer-gel electrolyte by mixing a polymer in a solution of an electrolyte in water to provide ionic conductivity.

A polymer gel may be a hydrophilic gel, and may include any one of polyethylene oxide, polyvinyl pyrrolidone and polyvinyl alcohol. The polymer electrolyte may include any one of zinc chloride, ammonium chloride, sodium chloride and combinations thereof.

The polymer-gel electrolyte 300 may be used in the form of being wetted to non-woven fabric or kraft paper because it has low mechanical strength.

Figure 5:
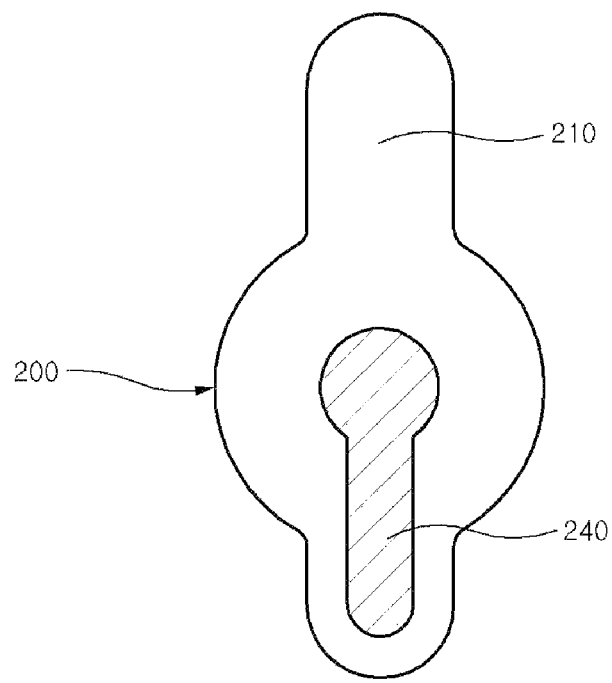
FIG. 5 is a plan view of a second electrode unit showing a collector.
Figure 6:
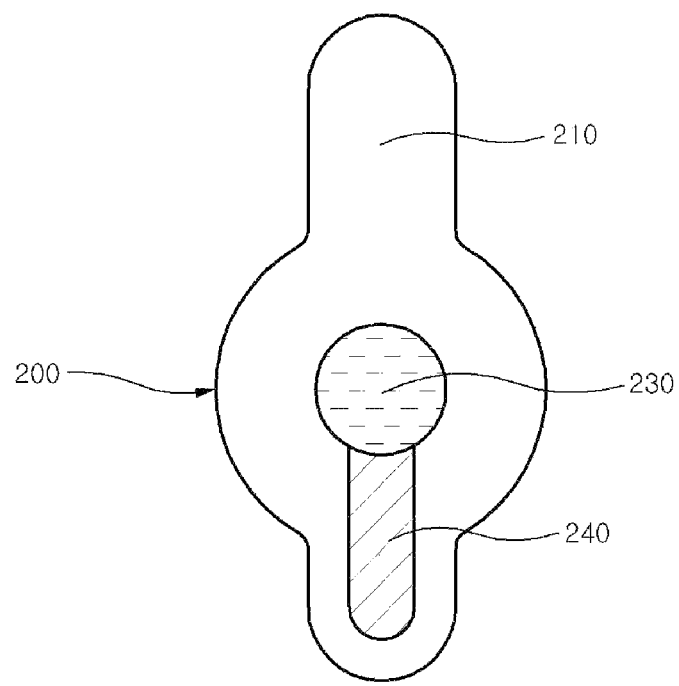
FIG. 6 is a plan view of a second electrode unit showing a second electrode layer.

FIG. 5 is a plan view showing a second electrode unit 200 including a collector 240 formed by coating a substrate 210 with carbon ink, and FIG. 6 is a plan view showing a second electrode unit 200 including a second electrode layer 230 formed by applying an anode composite material onto the collector 240.

The collector 240 serves to transfer electric current to a second electroconductive layer 220. The second electrode layer 230 is formed by applying an anode composite material onto the circular center portion of the collector 240 using a screen printing method.

The anode composite material includes zinc powder, carbon powder and a binder. Various anode active materials generating electric current were examined, but zinc powder may be preferably used as an anode active material for the sake of electric capacitance, voltage, electrochemical characteristics, product distribution environments, and the like.

The binder of the anode composite material, similarly to the binder of the cathode composite material, may include any one of polyethylene oxide, polyvinyl alcohol, polyvinyl pyrrolidone, polymethyl methacrylate and combinations thereof. In particular, as an anode binder, a combination of polyethylene oxide, polyvinyl pyrrolidone and polymethyl methacrylate is excellent in terms of electrical efficiency, processability and adhesivity.

The thickness of each of the cathode layer and the anode layer is determined in consideration of electrical capacitance and the like, and each of the cathode layer and the anode layer may have a thickness of 80~100 μm.

Figure 7:
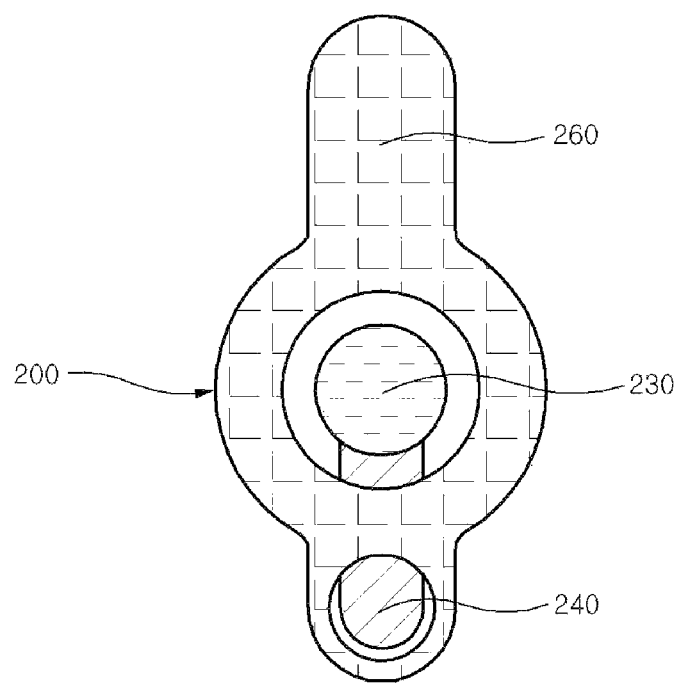
FIGS. 7 and 8 are plan views of a second electrode unit showing an electroconductive adhesive and an adhesive attached to a second electrode layer.
Figure 8:
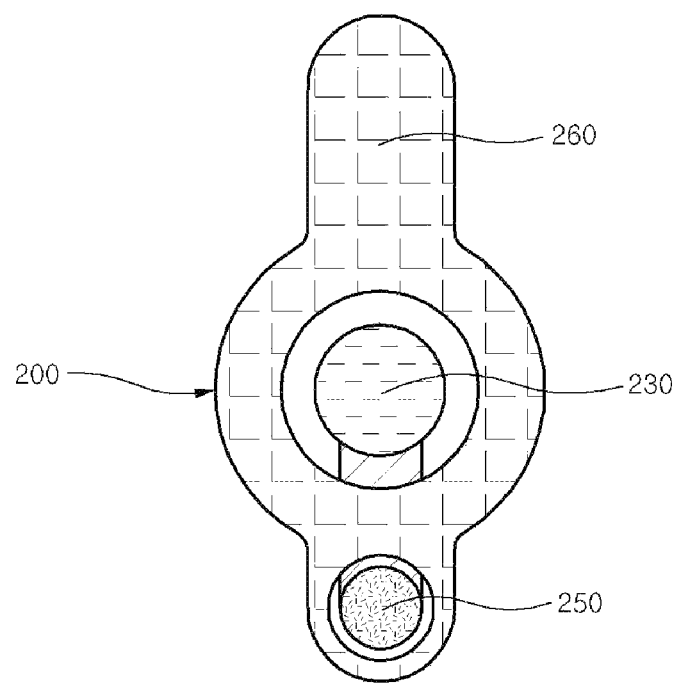

FIGS. 7 and 8 are plan views showing a second electrode unit 200 including an electroconductive adhesive 250 and an adhesive 260 attached to a second electrode layer 230. In FIGS. 7 and 8, a double-sided adhesive tape 260 surrounding the second electrode layer 230 is attached in order to preserve the polymer electrolyte 300 disposed between the first electrode layer 130 and the second electrode layer 230. The portions of the double-sided adhesive tape 260, which correspond to the second electrode layer 230 and the collector 240, were cut out, and then the second electrode layer 230 comes into contact with the first electrode layer 130 with the polymer electrolyte 300 disposed therebetween, and the collector 240 is coated with the electroconductive adhesive 250 to attach the second electrode layer 230 to the patch body, and thus the collector 240 comes into contact with second electroconductive layer 220. The electroconductive adhesive 250 may include any one of carbon powder, metal powder and combinations thereof.

The backing layer 140 may be formed of an insulating material, and, preferably, may be formed of a bendable insulating material such that its shape may vary depending on the shape of skin.

Although the preferred embodiments of the present invention have been described with reference to the limited examples together with the attached drawings, the terms and words used in the present specification and claims should not be interpreted as being limited to typical meanings or dictionary definitions, but should be interpreted as having meanings and concepts relevant to the technical scope of the present invention based on the rule according to which an inventor can appropriately define the concept of the term to describe the best method he or she knows for carrying out the invention. Therefore, those skilled in the art will appreciate that various modifications, additions and substitutions are possible, without departing from the scope and spirit of the invention as disclosed in the accompanying claims.

The invention claimed is:

1. A battery-integrated iontophoresis patch, comprising:
    a first electrode unit comprising:
        a first substrate having a variable shape;
        a first electroconductive layer disposed on the first substrate;
        a first electrode layer formed on the first electroconductive layer; and
        a second electroconductive layer disposed on the first substrate, the second electroconductive layer being electrically separated from the first electroconductive layer; and
    a second electrode unit comprising:
        a second substrate having a variable shape and facing the first substrate;
        a collector disposed on the second substrate, the collector being in electrical contact with the second electroconductive layer through an electroconductive adhesive; and
        a second electrode layer in electrical contact with the collector, the second electrode layer facing the first electrode layer and having a polarity opposite to that of the first electrode layer;
    an ion-conductive electrolyte disposed between the first electrode layer and the second electrode layer; and
    an adhesive for isolating the ion-conductive electrolyte from the first and second electroconductive layers.

2. The iontophoresis patch according to claim 1, wherein the first substrate or the second substrate is made of any one of polyethylene terephthalate and polyacrylonitrile.

3. The iontophoresis patch according to claim 1, wherein the first electroconductive layer includes any one of carbon powder and silver powder.

4. The iontophoresis patch according to claim 1, wherein the first electrode layer includes manganese dioxide powder, carbon powder and a binder.

5. The iontophoresis patch according to claim 4, wherein the binder includes any one of polyethylene oxide, polyvinyl alcohol, polyvinyl pyrrolidone, polymethyl methacrylate and combinations thereof.

6. The iontophoresis patch according to claim 1, wherein the second electroconductive layer includes any one of carbon powder, silver powder and nickel powder.

7. The iontophoresis patch according to claim 1, wherein the collector includes carbon powder.

8. The iontophoresis patch according to claim 1, wherein the adhesive is a double-sided adhesive tape.

9. The iontophoresis patch according to claim 1, wherein the second electrode layer includes zinc powder, carbon powder and a binder.

10. The iontophoresis patch according to claim 9, wherein the binder includes any one of polyethylene oxide, polyvinyl alcohol, polyvinyl pyrrolidone, polymethyl methacrylate and combinations thereof.

11. The iontophoresis patch according to claim 1, wherein the ion-conductive polymer electrolyte includes any one of zinc chloride, ammonium chloride, sodium chloride and combinations thereof.

12. The iontophoresis patch according to claim 1, wherein the electroconductive adhesive includes any one of carbon powder, metal powder and combinations thereof.

13. A battery-integrated iontophoresis patch, comprising:
    a first electrode unit comprising:
        a first substrate having a variable shape;
        a first electroconductive layer disposed on the first substrate;
        a first electrode layer formed on the first electroconductive layer; and
        a second electroconductive layer disposed on the first substrate, the second electroconductive layer being electrically separated from the first electroconductive layer; and
    a second electrode unit comprising:
        a second substrate having a variable shape and facing the first substrate;
        a collector disposed on the second substrate, the collector being in electrical contact with the second electroconductive layer through an electroconductive adhesive; and a second electrode layer in electrical contact with the collector, the second electrode layer facing the first electrode layer and having a polarity opposite to that of the first electrode layer;

an ion-conductive electrolyte disposed between the first electrode layer and the second electrode layer; and an adhesive layer disposed between the first and second substrates, the adhesive layer for sealing the ion-conductive electrolyte and attaching the second electrode unit to the first electrode unit.

14. The iontophoresis patch of claim 13, wherein the adhesive layer has a shape that is the same as the shape of the first substrate and is different from the shape of the second substrate.

15. The iontophoresis patch of claim 13, wherein the adhesive layer has a cut out for the ion-conductive electrolyte.

16. The iontophoresis patch of claim 13, wherein the adhesive layer has a cut out for the electroconductive adhesive.

17. The iontophoresis patch of claim 13, wherein the adhesive layer comprises a double-sided adhesive tape.

18. The iontophoresis patch of claim 13, wherein the electroconductive adhesive is for attaching the second electrode unit to the first electrode unit.

19. The iontophoresis patch of claim 13, wherein the shape of the first substrate is larger than the shape of the second substrate.

20. The iontophoresis patch of claim 13, wherein the ion-conductive electrolyte is disposed as a non-woven fabric or kraft paper wetted with the ion-conductive electrolyte.

\* \* \* \* \*